(12) United States Patent
Ghose et al.

(10) Patent No.: US 9,994,609 B2
(45) Date of Patent: Jun. 12, 2018

(54) HYDROPHOBIC INTERACTION PROTEIN CHROMATOGRAPHY UNDER NO-SALT CONDITIONS

(71) Applicant: Biogen MA Inc., Cambridge, MA (US)

(72) Inventors: Sanchayita Ghose, Morrisville, NC (US); Yinying Tao, Morrisville, NC (US)

(73) Assignee: Biogen MA Inc., Cambridge, MA (US)

( * ) Notice: Subject to any disclaimer, the term of this patent is extended or adjusted under 35 U.S.C. 154(b) by 294 days.

(21) Appl. No.: 14/775,774

(22) PCT Filed: Mar. 15, 2014

(86) PCT No.: PCT/US2014/029930
§ 371 (c)(1),
(2) Date: Sep. 14, 2015

(87) PCT Pub. No.: WO2014/145208
PCT Pub. Date: Sep. 18, 2014

(65) Prior Publication Data
US 2016/0024145 A1    Jan. 28, 2016

Related U.S. Application Data

(60) Provisional application No. 61/791,238, filed on Mar. 15, 2013.

(51) Int. Cl.
*C07K 1/20* (2006.01)
*C07K 16/06* (2006.01)

(52) U.S. Cl.
CPC .............. *C07K 1/20* (2013.01); *C07K 16/065* (2013.01)

(58) Field of Classification Search
None
See application file for complete search history.

(56) References Cited

U.S. PATENT DOCUMENTS 5,641,870 A * 6/1997 Rinderknecht ...... C07K 16/065
                                                          435/252.3
7,408,030 B2   8/2008 Carbonell et al.
8,273,707 B2   9/2012 Senczuk et al.
9,493,568 B2 * 11/2016 Reilly .............. A61K 47/48561
2005/0136521 A1 * 6/2005 Shukla .................... C07K 1/20
                                                              435/183
2011/0206687 A1  8/2011 Hickman
2012/0149878 A1  6/2012 Gillespie et al.
2012/0202976 A1  8/2012 Axen et al.
2013/0338344 A1 12/2013 Ramasubramanyan et al.
2016/0115193 A1 * 4/2016 Herigstad .............. C07K 16/00
                                                              424/142.1

FOREIGN PATENT DOCUMENTS

WO    WO 2007/071068 A1    6/2007

OTHER PUBLICATIONS

Sigma-Aldrich ToyoScreen HIC Mix Pack Process Development Column, pp. 1-3, copyright 2017.*
Sigma-Aldrich "Toyopearl Hexyl-650C Bulk Media" pp. 1-3, copyright 2017.*
International Search Report and Written Opinion for International Application No. PCT/US14/029930 dated Jul. 29, 2014.
International Preliminary Report on Patentability for International Application No. PCT/US14/029930 dated Sep. 24, 2015.
Supplemental European Search Report for European Patent Application No. EP 14765488.3 dated Oct. 14, 2016.
[No Author Listed] Tosoh Bioscience. Chromatographic Process Media Catalog. Toyopearl and TSH Gel Process Resins, 2012, pp. 1-58; Retrieved from the Internet: <URL: http://www.separations.eu.tosohbioscience.com/NR/rdonlyres/059B8C4F-BC82-4D84-AF3D-5807DFCAEB56/0/C11P10A_processcatalog.pdf > ; p. 35.
Chen et al., Comparison of standard and new generation hydrophobic interaction chromatography resins in the monoclonal antibody purification process. Journal of Chromatography. Dec. 2007;1177(2):272-281.
EP 14765488.3, Oct. 14, 2016, Supplementary European Search Report.
PCT/US14/029930, Jul. 29, 2014, International Search Report and Written Opinion.
PCT/US14/029930, Sep. 24, 2015, International Preliminary Report on Patentability.

* cited by examiner

*Primary Examiner* — Daniel E Kolker
*Assistant Examiner* — James L Rogers
(74) *Attorney, Agent, or Firm* — Wolf, Greenfield & Sacks, P.C.

(57) ABSTRACT

Various aspects and embodiments of the present disclosure relate to the purification antibodies by hydrophobic interaction chromatography under no-salt conditions.

17 Claims, 3 Drawing Sheets

HYDROPHOBIC INTERACTION PROTEIN CHROMATOGRAPHY UNDER NO-SALT CONDITIONS

RELATED APPLICATIONS

This application is a national stage filing under 35 U.S.C. § 371 of international application number PCT/US2014/029930, filed Mar. 15, 2014, which was published under PCT Article 21(2) in English and claims the benefit under 35 U.S.C. § 119(e) of U.S. provisional application No. 61/791,238, filed Mar. 15, 2013, each of which is herein incorporated by reference in its entirety.

FIELD OF THE INVENTION

The invention is in the field of protein purification.

BACKGROUND OF THE INVENTION

Hydrophobic interaction chromatography (HIC) is used as a polishing step in many monoclonal antibody purification processes (Shukla and Thommes, *Trends in Biotechnol* 28(5): 253-261, 2010). This mode of chromatography is particularly useful for aggregate removal and also provides clearance of other process-related impurities such as host cell protein, leached Protein A and endogenous viruses (McCue et al., *Bioprocess Biosys Eng* 31: 261-275, 2008; Shukla et al., *J Chromatogr A* 848: 28-39, 2006; Jiang et al., *Biotechnol Bioeng* 107(6): 985-997, 2010). HIC is based on interactions between hydrophobic (aliphatic or aromatic) ligands on the stationary phase with hydrophobic patches on the surface of the proteins. Interactions of proteins with hydrophobic ligands are usually promoted by kosmotropic salts such as ammonium sulfate, sodium citrate, potassium phosphate and others (Melander et al., *J Chromatogr A* 317: 67-85, 1984). Kosmotropic salts interact with water molecules to reduce solvation of the protein molecules in solution and to expose their hydrophobic patches to promote binding (Liu et al., *mAbs* 2(5): 480-499, 2010). Elution is usually facilitated by decreasing salt concentration and sometimes by using organic mobile phase modifiers.

SUMMARY OF THE INVENTION

Hydrophobic interaction chromatography (HIC) is limited in its use by the high concentrations of kosmotropic salts required to achieve the desired product separation from contaminants. These salts often pose a disposal concern in manufacturing facilities and, at times, can cause precipitation of the product. The present disclosure overcomes this limitation by providing, in part, a method of operating HIC in the flow through (FT) mode with no salt in the mobile phase. This HIC method is based on the recognition of surprising data showing that product yield and purity, comparable to those observed using existing HIC methods under high-salt conditions, can be achieved in the absence of salt using a highly hydrophobic chromatography resin with an aqueous mobile phase pH of about 5 to about 7.

Thus, in various aspects and embodiments, the disclosure provides methods and kits for purifying an antibody by subjecting an antibody in solution to hydrophobic interaction chromatography in flow through mode using a matrix containing hydrophobic ligands, wherein the solution does not contain salt and has a pH of about 5.0 to about 7.0.

In some aspects, the disclosure provides methods and kits for purifying an antibody by providing an antibody in a solution that does not contain salt and has a pH of about 5.0 to about 7.0, loading the solution onto a matrix containing hydrophobic ligands, and collecting a flow through fraction that contains the antibody.

In some embodiments, the pH of the solution is about 5.0 to about 6.5, about 5.0 to about 6.0, about 5.5 to about 7.0, or about 6.0 to about 7.0.

In some embodiments, the matrix comprises a hydroxylated methacrylic polymer, agarose or sepharose.

In some embodiments, the hydrophobic ligands are phenyl groups, butyl groups, hexyl groups or octyl groups. In some embodiments, the hydrophobic ligands are covalently bound to the matrix.

In some embodiments, the binding capacity for lysozyme of the matrix containing ligands is between 30 mg/ml and 55 mg/ml. In some embodiments, the binding capacity for lysozyme of the matrix containing ligands is about 33.2 mg/ml (or is equal to 33.2 mg/ml).

In some embodiments, the antibody is a monoclonal antibody or a polyclonal antibody. In some embodiments, the antibody is a human antibody, a mouse antibody or a chimeric antibody.

In some aspects, the disclosure provides methods and kits for purifying an antibody by subjecting an antibody in solution to hydrophobic interaction chromatography in flow through mode using a matrix containing hydrophobic ligands and having a binding capacity for lysozyme of 30 mg/ml to 55 mg/ml, wherein the solution does not contain salt and has a pH of about 5.0 to about 7.0.

In some aspects, the disclosure provides methods and kits for purifying an antibody by subjecting an antibody in solution to hydrophobic interaction chromatography in flow through mode using a hydroxylated methacrylic polymer matrix containing hexyl groups, wherein the solution does not contain salt and has a pH of about 5.0 to about 7.0.

These and other aspects of the invention are described in more detail herein.

The invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. For purposes of clarity, not every component may be labeled in every drawing. In the drawings.

DETAILED DESCRIPTION OF THE INVENTION

Figure 1:
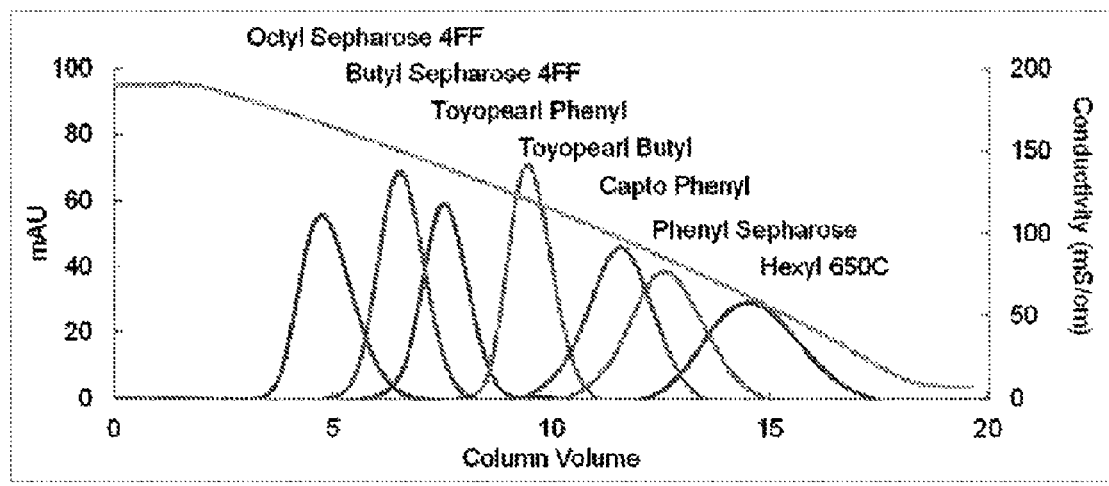
FIG. 1 shows a graph of linear retention of lysozyme for seven commercially available hydrophobic interaction chromatography (HIC) resins using a decreasing ammonium sulfate gradient.

Hydrophobic interaction chromatography (HIC) separates proteins according to differences in their surface hydrophobicity by utilizing a reversible interaction between these proteins and the hydrophobic surface of an HIC resin (e.g., polymeric matrix modified with hydrophobic ligands). Typically, the interaction between hydrophobic proteins and ligands of an HIC matrix is influenced by the presence of kosmotropic salts in the running buffer. A high salt concentration enhances the interaction, while lowering the salt concentration weakens the interaction. As the ionic strength of the buffer is reduced, the interaction between the protein and the matrix is reversed, and the protein with the lowest degree of hydrophobicity is eluted first. The most hydrophobic protein elutes last, requiring a greater reduction in salt concentration to reverse the interaction.

The use of a high concentration of salt is highly undesirable in many manufacturing processes because it causes corrosion of stainless steel tanks, and the most commonly used kosmotropic salt, ammonium sulfate, is expensive to dispose of due to municipal waste water concerns (Gagnon P., 2006, Polishing Methods for monoclonal IgG purification. In: Shukla A A, Etzel M R, Gadam S, editor. Process Scale Bioseparations for the Biopharmaceutical Industry. New York: Taylor & Francis. p 491-505). Further, the presence of salt in the load material, the flow through (FT) pool, and/or the elution pool during HIC complicates sample manipulation and requires significant dilution or ultrafiltration/diafiltration between processing steps (Chen et al., *J Chromatogr A* 1177: 272-2812008).

Despite the disadvantages associated with the use of high-salt in HIC, processes that circumvent this problem, while still providing for product yield and purity comparable to conventional HIC, have not been reported.

The present disclosure is based, at least in part, on the recognition of surprising data showing that product (e.g., antibody) yield and purity, comparable to those observed using existing HIC methods under high-salt conditions, can be achieved in the absence of salt using a highly hydrophobic chromatography resin with a solution pH of 5 to about 7. This data was unexpected in that (1) the effect of pH on protein/molecule retention in HIC is itself unpredictable and is not a parameter that is usually altered in HIC, and (2) typically, resins with hydrophobicity comparable to those used herein are not used for "bind and elute" applications because of the "too-strong" antibody-resin interactions, which result in low product recovery (see, e.g., Chen et al., *J Chromatogr A* 1177: 272-281, 2008).

Thus, the present disclosure provides, inter alia, methods of purifying a protein (e.g., antibody) using HIC under no-salt conditions.

Hydrophobic Interaction Chromatography

Hydrophobic interaction chromatography (HIC) separates molecules based on their hydrophobicity. HIC is a useful separation technique for purifying proteins while maintaining biological activity.

Most proteins, and to a much lesser extent hydrophilic molecules (e.g., DNA and carbohydrates), have hydrophobic areas or patches on their surface. Solvation of these patches is energetically unfavorable and results in the formation of hydrophobic cavities in the aqueous mobile phase. The promotion of the hydrophobic effect (by addition of kosmotropic salts) drives the adsorption of hydrophobic areas on a protein to the hydrophobic areas on the stationary phase (e.g., those areas of the matrix that contain hydrophobic ligands). This is thermodynamically favorable in that it reduces the number and volume of individual hydrophobic cavities. In conventional HIC, reducing hydrophobic interactions by decreasing the concentration of kosmotropic salts results in de-sorption from the solid support. Conventional HIC differs from other chromatographic separation methods in that proteins bind to the stationary phase at high salt concentration and elute at low salt concentration. This is manifested in a reverse salt gradient, which is an indication that conventional HIC is being used.

By contrast, the HIC methods provided herein are conducted in the absence of salt (e.g., salt other than that used to maintain the pH of a mobile phase buffer). The present disclosure provides HIC methods that include the use of a highly hydrophobic chromatography/HIC resin combined with an aqueous mobile phase buffer (referred to herein as a mobile phase buffer) having a pH of 5.0 to about 7.0 (or a pH of 5.0 to 7.0). A chromatography/HIC "resin," as used herein, refers to a matrix (e.g., polymeric matrix) having hydrophobic ligands immobilized thereon.

In an exemplary embodiment of the present disclosure, protein (e.g., unpurified or partially purified protein) is loaded onto a chromatography column, and then the loaded protein is "chased" by the addition of mobile phase buffer. In some embodiments, the protein may first be equilibrated in the mobile phase buffer prior to loading onto the column. In other embodiments, the protein is not equilibrated in mobile phase buffer prior to loading onto the column. The purified protein may be collected, for example, as flow-through fractions. Thus, unlike conventional HIC methods, methods of the present disclosure do not require multiple different buffers (e.g., binding buffers, washing buffers, elution buffers). The mobile phase buffer of the present disclosure, which contains, for example, less than 50 mM salt, may be used to equilibrate the chromatography column, to equilibrate the protein, and/or as a column flow-through buffer during the purification process and collection of purified protein.

Methods of the present disclosure use HIC in "flow-through mode." HIC in flow-through mode is often used to remove aggregates and other impurities. These impurities have chemical properties very similar to the target protein (e.g., antibody) but they are generally more hydrophobic than the target protein. Under appropriate conditions, such as those provided herein, impurities bind to the HIC resin of a column allowing target protein to flow through. Thus, "flow-through fractions," as used herein, refers to protein in mobile phase buffer, collected in fractions, that has passed through a column containing resin, as provided herein.

Several factors may be considered when choosing the ligands and matrix for an HIC resin. One such factor to consider is the type of ligand. HIC matrices maybe modified with (e.g., covalently bound by) hydrophobic ligand groups, to which hydrophobic areas of a protein adsorb. A protein's adsorption behavior is determined by the type of immobilized ligand. In general, straight chain alkyl ligands demonstrate hydrophobic character while aryl ligands show a mixed mode behavior where both aromatic and hydrophobic interactions are possible (Hofstee and Otillio, *J Chromatogr* 159, 57-69, 1978). The choice of ligand type may, in some instances, be empirically determined. Examples of hydrophobic ligands that may be used herein include, without limitation, ether groups, polypropylene glycol groups, phenyl groups, butyl groups, hexyl groups and octyl groups. Examples of HIC resins with these functional groups include, without limitation, Phenyl Sepharose, Butyl Sepharose, Octyl Sepharose, Capto Phenyl, Toyopearl Butyl, Toyopearl Phenyl, Toyopearl Hexyl, Toyopearl Ether, and Toyopearl PPG.

Another factor to consider is the degree of substitution. The protein binding capacity increases with an increased degree of substitution of the immobilized ligand. With a high level of ligand substitution, the binding capacity remains constant; however, the affinity of the interaction increases (Jennissen and Heilmeyer, *Biochemistry* 14, 754-760, 1975). Proteins bound under these conditions may be difficult to elute due to multi-point attachment (Jennissen, *J Chromatogr* 159, 71-83, 1978).

Yet another factor to consider is the type of matrix. The most widely used matrices are hydrophilic carbohydrates: cross-linked agarose and synthetic copolymer materials. The selectivity between different matrices will not be identical though the ligands may be the same. Examples of matrices that may be used in accordance with the present disclosure include, without limitation, agarose, sepharose and hydroxylated methacrylic polymers.

The hydrophobicity of an HIC resin may be assessed based on a measure of its retention of lysozyme, also referred to herein as the resin's "binding capacity for lysozyme." The assay used to obtain the values for a resin's binding capacity for lysozyme employs a mobile phase buffer solution that contains salt. In particular, the buffer solution used to obtain the values listed herein contained a salt concentration (e.g., sodium citrate, ammonium sulfate, sodium sulfate, sodium chloride, potassium chloride, phosphate or carbonate) of about 1 mol/L to about 3 mol/L of buffer solution. It is to be understood that while these binding capacity values are used to characterize the general hydrophobicity of a resin, the conditions under which these values were obtained are not the conditions that are contemplated for use in the methods provided by the present disclosure. Thus, in some embodiments provided herein, the binding capacity for lysozyme of a resin may be between 30 mg/ml and 55 mg/ml, or between 30 mg/ml and 35 mg/ml. For example, in some embodiments, the binding capacity for lysozyme may be about 30 mg/ml, about 35 mg/ml, about 40 mg/ml, about 45 mg/ml, about 50 mg/ml or about 55 mg/ml. In some embodiments, the binding capacity for lysozyme is 30.0 mg/ml, 30.1 mg/ml, 30.2 mg/ml, 30.3 mg/ml, 30.4 mg/ml, 30.5 mg/ml, 30.6 mg/ml, 30.6 mg/ml, 30.7 mg/ml, 30.8 mg/ml, 30.9 mg/ml, 31.0 mg/ml, 31.1 mg/ml, 31.2 mg/ml, 31.3 mg/ml, 31.4 mg/ml, 31.5 mg/ml, 31.6 mg/ml, 31.7 mg/ml, 31.8 mg/ml, 31.9 mg/ml, 32.0 mg/ml, 32.1 mg/ml, 32.2 mg/ml, 32.3 mg/ml, 32.4 mg/ml, 32.5 mg/ml, 32.6 mg/ml, 32.7 mg/ml, 32.8 mg/ml, 32.9 mg/ml, 33.0 mg/ml, 33.1 mg/ml, 33.2 mg/ml, 33.3 mg/ml, 33.4 mg/ml, 33.5 mg/ml, 33.6 mg/ml, 33.7 mg/ml, 33.8 mg/ml, 33.9 mg/ml, 34.0 mg/ml, 34.1 mg/ml, 34.2 mg/ml, 34.3 mg/ml, 34.4 mg/ml, 34.5 mg/ml, 34.6 mg/ml, 34.7 mg/ml, 34.8 mg/ml, 34.9 mg/ml, or 35.0 mg/ml. In some embodiments, the binding capacity for lysozyme of a resin may be lower than 30 mg/ml or higher than 55 mg/ml. Thus, methods provided herein may utilize an HIC resin having a binding capacity for lysozyme of any of the foregoing values. For example, a method of the present disclosure may utilize an HIC resin having a hydroxylated methacrylic polymer matrix containing hexyl groups and a binding capacity of about 30 mg/ml to about 35 mg/ml, or about 33 mg/ml.

Surprisingly, the present disclosure shows that rather than using salt to regulate the interaction between hydrophobic areas on a protein (e.g., antibody) and hydrophobic areas on a matrix (e.g., containing resin), the pH of a mobile phase buffer can be modified to serve a similar purpose, but without the adverse effects of high salt (e.g., greater than 50 mM salt, or greater than 100 mM salt). The pH of the solutions in a mobile phase provided herein may be between 5.0 and 7.0, or between 5.0 and about 7.0 (e.g., including endpoints 5.0 and about 7.0), between 5.0 and about 6.5 (e.g., including endpoints 5.0 and about 6.5), between 5.0 and about 6.0 (e.g., including endpoints 5.0 and about 6.0), between 5.5 and about 7.0 (e.g., including endpoints 5.5 and about 7.0), between 5.5 and about 6.5 (e.g., including endpoints 5.5 and about 6.5), or between 5.5 and about 6.0 (e.g., including endpoints 5.5 and about 6.0). For example, in some embodiments, the pH of the solution in the mobile phase may be 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0.

Methods provided herein are considered to be "salt-free" or conducted under "no-salt conditions" if salt is not added to the HIC system (e.g., aqueous buffers, such as mobile phase buffers, used in the HIC system). It should be appreciated that buffers used to maintain the pH of solutions used for protein purification may contain low concentrations of salts in some embodiments. Buffers (e.g., pH buffers) typically contain, for example, a mixture of a weak acid and its conjugate base. Examples of buffering components include, without limitation, citric acid/sodium citrate, acetic acid, $KH_2PO_4$, N-Cyclohexyl-2-aminoethanesulfonic acid (CHES) and borate. In some embodiments, a buffer (e.g., mobile phase buffer) may include a 100 mM or less (e.g., 50 mM or less, 25 mM or less, 20 mM or less, 15 mM or less, 10 mM or less, 5 mM or less, 2.5 mM or less, or intermediate concentrations) of one or more buffer components (e.g., sodium citrate) that are used in the buffer solution. In some embodiments, mobile phase buffers of the present disclosure have a conductivity of 1 milli-Siemens/centimeter (mS/cm) to 10 mS/cm. In some embodiments, mobile phase buffers of the present disclosure have a conductivity of less than 10 mS/cm. For example, mobile phase buffers of the present disclosure may have a conductivity of 9 mS/cm (or less than 9 mS/cm), 8 mS/cm (or less than 8 mS/cm), 7 mS/cm (or less than 7 mS/cm), 6 mS/cm (or less than 6 mS/cm), 5 mS/cm (or less than 5 mS/cm), 4 mS/cm (or less than 4 mS/cm), 3 mS/cm (or less than 3 mS/cm), 2 mS/cm (or less than 2 mS/cm), or 1 mS/cm (or less than 1 mS/cm).

In some embodiments, a mobile phase buffer includes sodium citrate as a pH buffering component. In some embodiments, sodium citrate is present in a mobile phase buffer at a concentration of 3 mM to 20 mM. For example, sodium citrate may be present in a mobile phase buffer at a concentration of 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM or 20 mM. In some embodiments, sodium citrate is present in a mobile phase buffer at a concentration of 5 mM to 10 mM. In some embodiments, protein is loaded onto an HIC column, followed by the addition of mobile phase buffer to the column. In some embodiments, purified protein is collected from flow-through fractions. It should be appreciated that in other embodiments, alternative buffers (e.g., as described herein) may be used at similar concentrations instead of sodium citrate.

It is to be understood that there may be a small amount of salt (e.g., NaCl) present in the protein sample to be purified, as such salt is typically used in storage buffers for soluble protein stabilization.

In some embodiments, chromatography columns are equilibrated with 1 to 15 column volumes of mobile phase buffer. For example, in some embodiments, chromatography columns are equilibrated with 1, 2, 3, 4, 5, 6, 7, 8, 9, 10, 1, 12, 13, 14 or 15 column volumes of mobile phase buffer. In some embodiments, chromatography columns are equilibrated with less than 1 or more than 15 column volumes of mobile phase buffer. In some embodiments, a column volume is 5 ml to 50 ml, or more. For example, a column volume may be 5 ml, 10 ml, 15 ml, 20 ml, 25 ml, 30 ml, 35 ml, 40 ml, 45 ml or 50 ml. A column volume may be scaled up or down, depending on the application. For example, large-scale applications may utilize greater column volumes.

In some embodiments, a column residence time is of 2 minutes to 10 minutes. As used herein, "residence time" refers to the average amount of time that a particle (e.g., protein or impurity) spends in a particular system (e.g., column). In some embodiments, a column residence time is 2 min, 3 min, 4 min, 5 min, 6 min, 7 min, 8 min, 9 min or 10 min. In some embodiments, a column residence time is 6 min.

In some embodiments, a first purification, or "polishing," step is used, followed by a second HIC FT purification step, as provided herein. The first polishing step may include purification of a protein using ion exchange chromatography such as, for example, anion exchange (AEX) chromatography (e.g., using a TMAE FRACTOGEL®). It should be appreciated that other purification methods may be used, in some embodiments, as a first polishing step. In some embodiments, an HIC FT method of the present disclosure is used as a first (and, in some instances, the only) polishing step. Thus, methods of the present disclosure do not require a first polishing step different from salt-free HIC FT methods provided herein.

In some embodiments, the purified protein is concentrated, for example, by ultrafiltration (UF) and/or diafiltration (DF).

Antibodies

Methods provided herein are particularly useful for purifying antibodies. An antibody (interchangeably used in plural form) is an immunoglobulin molecule capable of specific binding to a target such as, for example, a carbohydrate, polynucleotide, lipid or polypeptide through at least one antigen recognition site located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')$_2$ and Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of a required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins may be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1 and IgA2. In some embodiments, an antibody of the present disclosure is an IgG1 antibody. The heavy-chain constant domains that correspond to the different classes of immunoglobulins are called alpha, delta, epsilon, gamma and mu, respectively. The subunit structures and three-dimensional configurations of different classes of immunoglobulins are well known.

Antibodies that may be purified using the HIC methods provided herein may be either monoclonal or polyclonal. A "monoclonal antibody" refers to a homogenous antibody population, and a "polyclonal antibody" refers to a heterogeneous antibody population.

In some embodiments, the antibodies are humanized antibodies. Humanized antibodies may refer to forms of non-human (e.g., murine) antibodies that are specific chimeric immunoglobulins, immunoglobulin chains or antigen-binding fragments thereof that contain minimal sequence derived from non-human immunoglobulin. Humanized antibodies may be human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity.

In some embodiments, the antibodies are chimeric antibodies, which can include a heavy constant region and a light constant region from human antibodies. Chimeric antibodies may refer to antibodies having a variable region or part of variable region from a first species and a constant region from a second species.

Examples of antibodies that may be purified using the HIC methods provided herein include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab, Tildrakizumab, Tigatuzumab, TNX-, Tocilizumab, Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

In some embodiments, an antibody is selected from anti-alpha synuclein (A-SYN) (see, e.g., Publication No. WO2012177972A1, incorporated by reference herein), anti-BART (see, e.g., Publication No. WO2008081008A1 and Publication No. US20110182809, each incorporated by reference herein) and anti-LINGO (see, e.g., U.S. Pat. No. 8,425,910B2 and Publication No. US20120014960A1, each incorporated by reference herein).

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced herein.

Example

This study was directed to identifying an alternative hydrophobic interaction chromatography (HIC) flow through (FT) step under no-salt conditions that would be comparable in process performance to the existing high-salt HIC FT step (control).

Four monoclonal antibodies (mAbs A-D; e.g., A-SYN, BART, LINGO, and a further monoclonal antibody, respectively) were used in this study, each with varying pIs (~6.5-8.5) and surface hydrophobicity as determined by linear retention on HIC resin. All of these antibodies had an HIC FT step in their manufacturing process, which primarily served to reduce aggregates and host cell proteins. Ammonium sulfate was used as the kosmotropic salt to achieve the desired selectivity, and the concentration selected in the process was dependent on the hydrophobicity of the molecule and the separation desired. Table 1 shows the ammonium sulfate concentration needed for each molecule and the dilution that was required to prepare the load sample for its respective HIC (Phenyl Sepharose Fast Flow (FF) High Substitution (HS)) FT step.

TABLE 1

Ammonium sulfate concentrations used in the control HIC FT processes and corresponding dilutions with high salt solution required to achieve the required conductivity

| Molecule | Ammonium sulfate concentration needed in the existing HIC process | % Dilution needed to achieve the needed salt concentration |
|---|---|---|
| A | 200 mM | 14 |
| B | 650 mM | 33 |
| C | 220 mM | 26 |
| D | Control HIC process did not exist | |

Resin Selection.

To create a no-salt HIC FT step, the following commercially-available resins (matrix containing hydrophobic ligands) were selected and their hydrophobicity compared: Capto Phenyl (High Sub), Butyl Sepharose 4 Fast Flow (FF), and Octyl Sepharose 4 FF (GE Healthcare Life Sciences); and Toyopearl Phenyl-650M, Toyopearl Butyl-650M and Toyopearl Hexyl-650C (Tosoh Bioscience, LLC). Existing HIC methods typically use a phenyl sepharose matrix (e.g., Phenyl Sepharose FF HS), which was used in this study as a control resin. To compare the hydrophobicity of various matrices, linear retention of lysozyme in a decreasing salt (ammonium sulfate) gradient was determined on each HIC resins. More hydrophobic ligands, e.g., phenyl, butyl, hexyl, octyl, were selected for this experiment, and less hydrophobic ligands such as ether and PPG were excluded. FIG. 1 shows the linear retention data for each of the matrices tested. As shown, Hexyl Toyopearl Hexyl-650C was more hydrophobic than the control, Phenyl Sepharose FF HS and, thus, was selected for further analysis. Hexyl Toyopearl Hexyl-650C resin also offers the advantage of a rigid polymeric backbone and permits faster flow rate and ease of packing at larger scale.

pH Selection.

Figure 2:
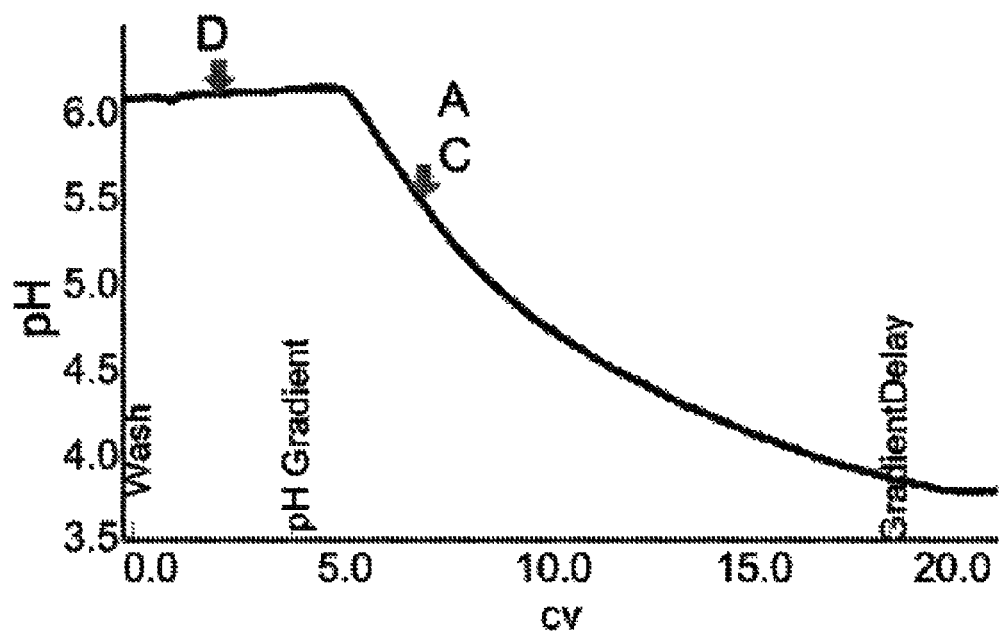
FIG. 2 shows a graph of linear retention of mAbs A-D on Hexyl Toyopearl in a decreasing pH gradient.

To identify the pH of the mobile phase needed for the FT step, pH gradients were run under analytical conditions on the Toyopearl Hexyl-650C resin with all four antibodies. The pH at which each mAb eluted in the gradient is shown in FIG. 2 and the exact values are listed in Table 2. The amount of protein loaded during the FT step was kept the same as the control process. Using the mobile phase pH identified, results showed that product yield and impurity clearance were comparable to the control. It was found that both pI and surface hydrophobicity of the antibodies were factors in determining optimal pH.

TABLE 2

Elution pH at peak maxima in a decreasing pH gradient on Hexyl Toyopearl data

| | pH at peak maxima |
|---|---|
| A | 5.5 |
| B | 6.0 |
| C | 5.6 |
| D | 6.0 |

*Elution pH of 6.0 implies the antibody was un-retained in the gradient

Figure 3:
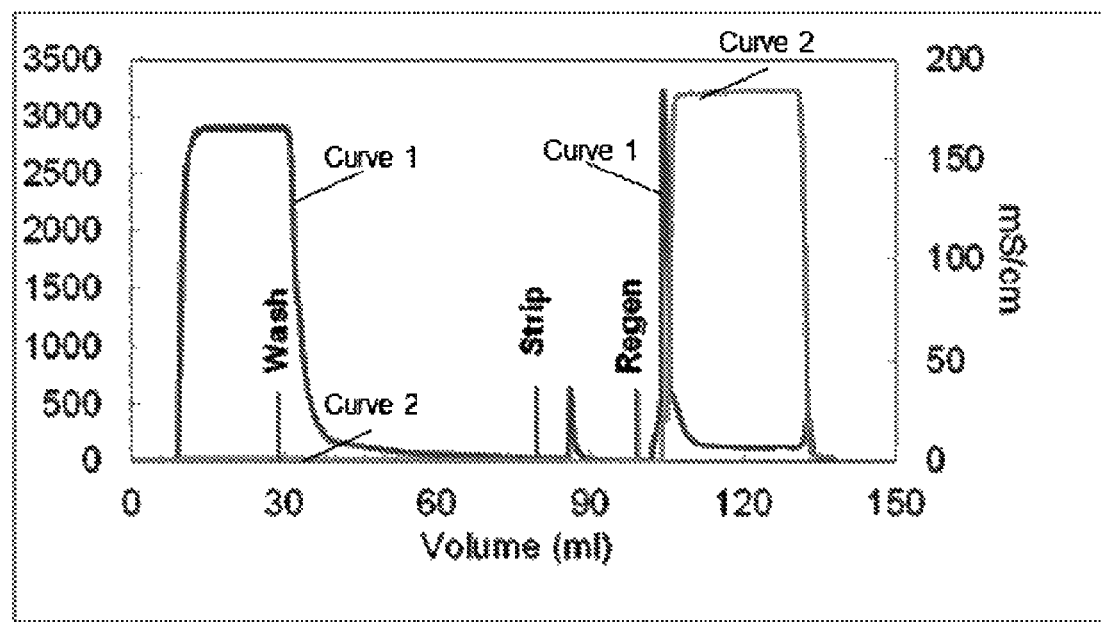
FIG. 3 shows a representative chromatogram for a no-salt HIC FT step of the present disclosure.

FIG. 3 shows a representative chromatogram for mAb B from the no-salt HIC flow-through step. Table 3 lists the final conditions developed for isolating proteins (e.g., antibodies) using an HIC FT step under no-salt conditions.

TABLE 3

Process performance comparison between high-salt and no-salt HIC FT step for each antibody

| mAb | Loading HIC FT g/L | HIC FT condition | Mobile phase composition | Mobile phase cond ms/cm | Step Yield % | Product Quality in FT pool | |
|---|---|---|---|---|---|---|---|
| | | | | | | HMW % | HCP level ppm |
| A | | | Load - Eluate from the first polishing step | | | 0.8 | 10 |
| | 35 | Control | 200 mM AmSO4 in 50 mM sodium acetate pH 5.2 | 39 | 85 | 0.33 | <3 |
| | | No salt | 10 mM sodium citrate, pH 5.5 | 2.6 | 86 | 0.21 | 3.8 |
| B | | | Load - Eluate from the first polishing step | | | 0.7 | 25 |
| | 65 | Control | 650 mM AmSO4 in 20 mM sodium acetate pH 5.6 | 95 | 78 | 0.10 | 4.8 |
| | | No salt | 5 mM sodium citrate, pH 6.0 | 1.3 | 88 | 0.13 | 4.7 |
| C* | | | Load - Eluate from capture step | | | 2.5 | 100 |
| | 70 | Control | 220 mM AmSO4 in 50 mM sodium acetate pH 5.5 | 38 | 86 | 0.31 | 38 |
| | | No salt | 10 mM sodium citrate, pH 5.5 | 2.6 | 88 | 0.34 | 23 |
| D | | | Load - Eluate from the first polishing step | | | 2.2 | 10 |
| | 55 | Control** | — | — | — | — | — |
| | | No salt | 10 mM sodium citrate, pH 6.0 | 2.6 | 90 | 0.37 | <1.4 |

Figure 4:
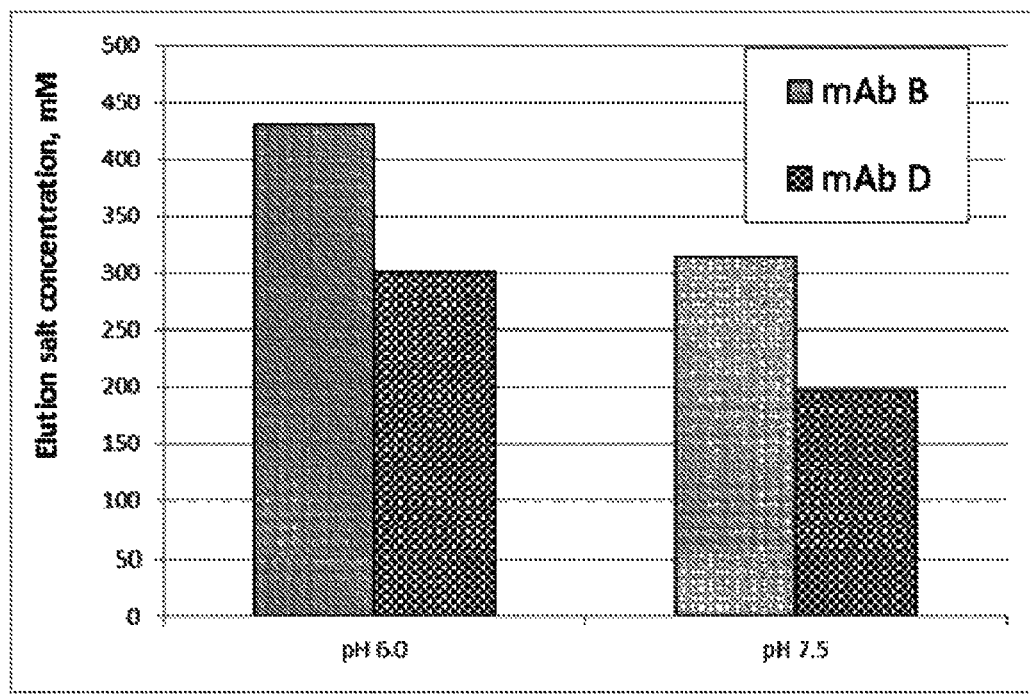
FIG. 4 shows a graph of the elution salt concentration of mAb B and D on a decreasing ammonium sulfate gradient using Phenyl Toyopearl resin (lower elution salt concentration implies greater hydrophobicity).

*HIC used as the $2^{nd}$ polishing step for mAb A, B, D and as the $1^{st}$ step for mAb C
**Control HIC process did not exist for mAb D, only the new low salt HIC step was developed
Abbreviations: AmSO4, ammonium sulfate; FT, flowthrough; HCP, host cell protein; HMW, high molecular weight; cond, conductivity A comparison of the data in Tables 2 and 3 shows that the optimum pH conditions were similar to those obtained from the analytical pH gradient experiments. Unexpectedly, mAbs B and D had the same optimum pH (pH 6.0) despite having pIs at the two ends of the range (8.7 vs. 6.5). This may be a result of the difference in surface hydrophobicity between the two antibodies, as determined by linear retention on the control HIC resin (FIG. 4). MAb B is less hydrophobic than mAb D (FIG. 4), which may have counteracted the effect of higher pI. Thus, the optimum pH needed by each molecule was influenced by both its pI and surface hydrophobicity. As shown in Table 3, the process data (step recovery and impurity clearance) from the two HIC steps (no-salt and high salt control process) indicates that performance comparable to the control was observed in all cases.

Figure 5:
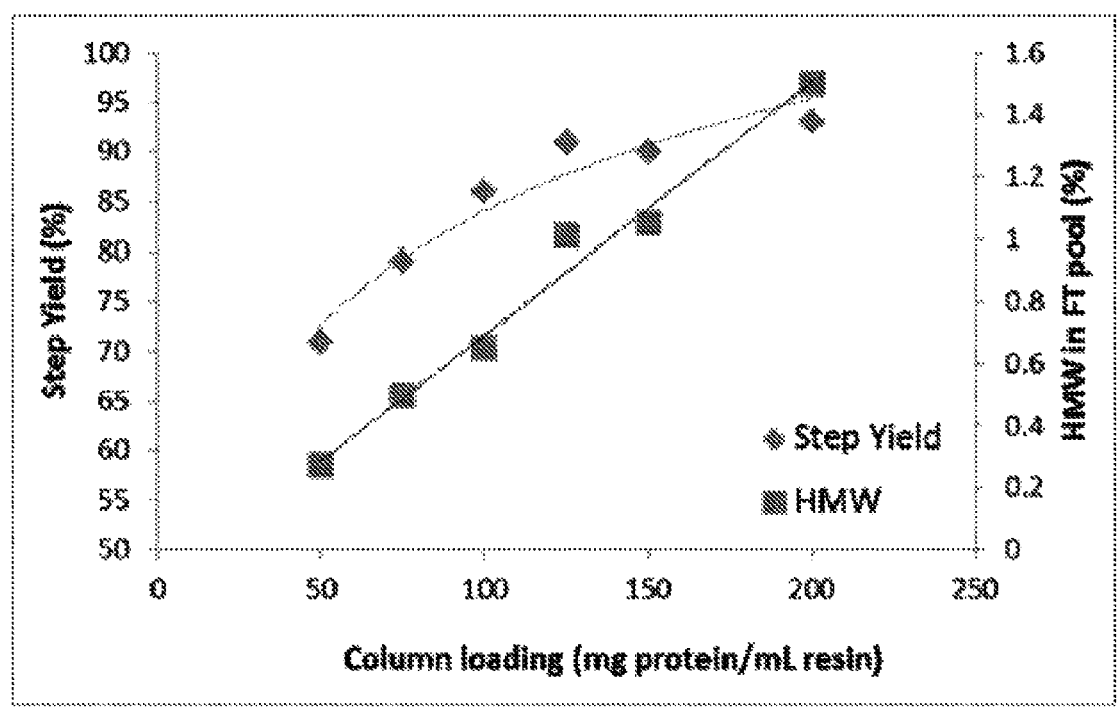
FIG. 5 shows a graph of the effect of column loading on the performance of a no-salt HIC FT step of the present disclosure.

Further studies were conducted with mAb B to evaluate the effect of column loading on step performance. FIG. 5 plots step yield and HMW level of the FT pool as a function of column loading on the Hexyl resin. Only HMW was monitored as it was the critical impurity that needed to be removed by this step. Protein A eluate with a higher HMW % was used for this analysis, thus the HMW levels are higher than that reported in Table 3. FIG. 5 shows that both yield and HMW levels increased as a function of column loading. This is typical for any flow-through step where the optimum column loading is selected based on best compromise between yield and desired HMW level. The rate of increase in this case was found to be similar to what had been seen with the historic high salt HIC step. An average loading of ~100 g/L was chosen for this process to consistently meet target HMW level of <1%.

After finalizing the mobile phase conditions and column loading, a resin lot to lot variability was also completed to ensure process robustness at manufacturing scale (Table 4). This was considered important since resin hydrophobicity was a major contributor to the selectivity of this step. Three lots of Hexyl resin spanning across the manufacturer's specification range was chosen for this study. Since the HIC step was designed to be used as the $2^{nd}$ polishing step, eluate from the $1^{st}$ polishing step (using anion exchange chromatography with TMAE FRACTOGEL®) was used as load for this study. All experiments were performed at 100 mg/ml resin loading. Table 4 summarizes the yield and product quality data and shows consistent performance across all three resin lots.

TABLE 4

Resin lot-to-lot variability study

| | Step yield % | HMW % | HCP level ppm |
|---|---|---|---|
| Load material | — | 0.6 | 11 |
| Resin Lot 65HECB501H | 93 | 0.28 | 0.8 |
| Resin Lot 65HECB01P | 92 | 0.26 | 0.8 |
| Resin Lot 65HECB501N | 95 | 0.26 | 1.4 |

The results of this study were unexpected in that, for example, (1) the effect of pH on retention in HIC is itself unpredictable, and (2) typically resins with such high hydrophobicity, e.g., Toyopearl Hexyl-650C, are not used for "bind and elute" applications because of the too-strong antibody-resin interactions, which result in low product recovery (see, e.g., Chen et al., *J Chromatogr A* 1177: 272-281, 2008).

Operating an HIC FT step without salt has tremendous implications for any large scale process. For example, it eliminates the need for any dilution (due to the addition of high salt) prior to the HIC FT step and enables facility fit upon scale up by overcoming tank volume limitations. Minimizing pool volume through the process also had an economic impact as it helps to reduce the size of the costly viral filter that follows the HIC FT step. Removing salt (e.g., ammonium sulfate) from the manufacturing process reduces disposal costs and is considered more manufacturing friendly.

Materials and Methods

Materials

All mAbs used in this study were produced in a CHO cell line. MAbs A-D were IgG1s with isoelectric points of ~7.2, 8.7, 7.4 and 6.5, respectively. Model protein lysozyme was purchased from Sigma (St. Louis, Mo.). Agarose-based resins such as Phenyl Sepharose HS, Capto Phenyl HS, Butyl Sepharose 4FF and Octyl Sepharose 4FF were obtained from GE Healthcare (Piscataway, N.J.). Methacrylate-based HIC resins such as Phenyl Toyopearl 650M, Butyl Toyopearl 650M and Hexyl Toyopearl 650C were obtained from Tosoh Bioscience (Montgomeryville, Pa.). TSK gel G3000 SWXL column (7.8 mm×300 mm) used for SEC analysis was purchased from Tosoh Bioscience (Montgomeryville, Pa.). All chemicals and salts were purchased from JT Baker (Phillipsburg, N.J.).

Equipment

All chromatographic experiments were carried out on AKTA Explorer chromatographic systems from GE Healthcare (Uppsala, Sweden). HPLC analysis was carried out in a Waters (Milford, Mass.) HPLC e2695 Separation Module. Absorbance of protein samples was measured using a Lambda 25 UV/VIS spectrophotometer from Perkin Elmer (Waltham, Mass.).

Protein Retention Experiments

Linear retention data of lysozyme on the various HIC resins was obtained from linear gradient experiments using pulse injection (0.1 mL of protein at ~5 mg/ml concentration) using a 0.66 cm D×10 cm L column. A decreasing gradient of salt (ammonium sulfate) was run from 1.5 M to 0 M over 15 column volumes in a phosphate buffer system at pH 7.0.

The elution pH of the various antibodies on Hexyl Toyopearl was obtained from linear gradient experiments using pulse injection (0.5 mL of protein at ~5 mg/ml concentration) using a 0.66 cm D×10 cm L column. A decreasing gradient of pH was run from pH 6.0 to 3.5 over 15 column volumes in a 10 mM citrate (conductivity ~2-3 mS/cm) buffer system. The elution pH at peak maxima was calculated from the gradient and further verified from the effluent pH trace obtained from the online Monitor pH/C-900 unit that is part of the AKTA system.

Salt gradient experiments with mAbs B and D were also performed in a similar manner on the Phenyl Sepharose resin. A decreasing gradient of ammonium sulfate was run from 1.5 to 0 M ammonium sulfate at pHs 6 and 7 over 10 column volumes. The elution salt concentration at peak maxima was calculated from the gradient.

Preparative Purification Experiments

The HIC preparative experiments were performed in the flow-through mode. A 1 cm D×20 cm L column was used for each experiment. The column was first equilibrated with 3 column volumes of the mobile phase (e.g., equilibration) buffer. The mobile phase salt concentration and pH of that buffer was specific to the protein and resin combination, as explained in the Results section. The column was then loaded with a specific amount of protein as mentioned above. The flow-through peak collection was started as the UV started to rise and the product was chased with the mobile phase (e.g., equilibration) buffer. The column was cleaned/washed with 3-5 column volumes of water and sanitized with 0.5N NaOH. A residence time of 6 minutes was used throughout the process.

Analytical Techniques

HMW levels in samples were measured by analytical Size Exclusion Chromatography (SEC) using TSK gel G3000 SWXL column. A mobile phase of 100 mM NaPO4, 200 mM NaCl, pH 6.8 and a flow rate of 1 mL/min was used. Elution peaks were detected by UV absorbance at 280 nm.

HCP levels in the samples from the preparative experiments were determined using an in-house generic HCP assay comprising an ELISA-based immunoassay using electrochemiluminescent detection on the Meso Scale Discovery platform.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of purifying an antibody, the method comprising:
   subjecting an antibody in solution to hydrophobic interaction chromatography in flow through mode using a matrix comprising a hydroxylated methacrylic polymer containing hexyl groups, wherein the solution does not contain an ammonium sulfate salt and has a pH of about 5.0 to about 7.0.

2. The method of claim 1, wherein matrix has a binding capacity for lysozyme of between 30 mg/ml and 50 mg/ml.

3. The method of claim 1, wherein the pH of the solution is about 5.0 to about 6.5, about 5.0 to about 6.0, about 5.5 to about 7.0, or about 6.0 to about 7.0.

4. The method of claim 1, wherein the antibody is a monoclonal antibody or a polyclonal antibody.

5. The method of claim 4, wherein the antibody is a human antibody, a mouse antibody or a chimeric antibody.

6. A method of purifying an antibody, the method comprising:
   providing an antibody in a solution that does not contain an ammonium sulfate salt and has a pH of about 5.0 to about 7.0;
   loading the solution onto a matrix comprising a hydroxylated methacrylic polymer containing hexyl groups; and
   collecting a flow through fraction that contains the antibody.

7. The method of claim 6, wherein matrix has a binding capacity for lysozyme of between 30 mg/ml and 50 mg/ml.

8. A method of purifying an antibody, the method comprising:
   subjecting an antibody in solution to hydrophobic interaction chromatography in flow through mode using a hydroxylated methacrylic polymer matrix containing hexyl groups, wherein the solution does not contain a kosmotropic salt and has a pH of about 5.0 to about 7.0.

9. The method of claim 8, wherein the pH of the solution is about 5.0 to about 6.5, about 5.0 to about 6.0, about 5.5 to about 7.0, or about 6.0 to about 7.0.

10. The method of claim 8, wherein the antibody is a monoclonal antibody or a polyclonal antibody.

11. The method of claim 10, wherein the antibody is a human antibody, a mouse antibody or a chimeric antibody.

12. The method of claim 8, wherein matrix has a binding capacity for lysozyme of between 30 mg/ml and 50 mg/ml.

13. A method of purifying an antibody, the method comprising:
    providing an antibody in a solution that does not contain a kosmotropic salt and has a pH of about 5.0 to about 7.0;
    loading the solution onto a hydroxylated methacrylic polymer matrix containing hexyl groups; and
    collecting a flow through fraction that contains the antibody.

14. The method of claim 13, wherein matrix has a binding capacity for lysozyme of between 30 mg/ml and 50 mg/ml.

15. The method of claim 13, wherein the pH of the solution is about 5.0 to about 6.5, about 5.0 to about 6.0, about 5.5 to about 7.0, or about 6.0 to about 7.0.

16. The method of claim 13, wherein the antibody is a monoclonal antibody or a polyclonal antibody.

17. The method of claim 16, wherein the antibody is a human antibody, a mouse antibody or a chimeric antibody.

\* \* \* \* \*